US010815032B2

(12) United States Patent
Vouillamoz

(10) Patent No.: US 10,815,032 B2
(45) Date of Patent: Oct. 27, 2020

(54) COMPENSATED CAPILLARY INDICATOR

(71) Applicant: Preciflex SA, Neuchâtel (CH)

(72) Inventor: Lucien Vouillamoz, Feusisberg (CH)

(73) Assignee: PRECIFLEX SA, Neuchâtel (CH)

( * ) Notice: Subject to any disclaimer, the term of this patent is extended or adjusted under 35 U.S.C. 154(b) by 496 days.

(21) Appl. No.: 14/391,395

(22) PCT Filed: Apr. 12, 2013

(86) PCT No.: PCT/IB2013/000660
§ 371 (c)(1),
(2) Date: Oct. 9, 2014

(87) PCT Pub. No.: WO2013/153436
PCT Pub. Date: Oct. 17, 2013

(65) Prior Publication Data
US 2015/0098665 A1 Apr. 9, 2015

Related U.S. Application Data

(60) Provisional application No. 61/793,013, filed on Mar. 15, 2013, provisional application No. 61/623,160, filed on Apr. 12, 2012.

(51) Int. Cl.
*G04B 25/00* (2006.01)
*B65D 30/22* (2006.01)
(Continued)

(52) U.S. Cl.
CPC .............. *B65D 31/12* (2013.01); *G04B 1/265* (2013.01); *G04B 25/00* (2013.01); *A61M 5/141* (2013.01)

(58) Field of Classification Search
CPC ........ B65D 31/12; G04B 1/265; G04B 25/00; A61M 5/1454; A61M 5/141
See application file for complete search history.

(56) References Cited

U.S. PATENT DOCUMENTS 3,595,329 A * 7/1971 Withnell ................... B07C 5/32
177/1
3,908,461 A * 9/1975 Turpen ................. G01L 9/0035
338/41
(Continued)

FOREIGN PATENT DOCUMENTS

FR          1552838       1/1969
WO          WO 87/04629   8/1987

OTHER PUBLICATIONS

International patent application No. PCT/IB2013/000660, International Search Report, dated Oct. 17, 2013.
(Continued)

*Primary Examiner* — Abiy Teka
(74) *Attorney, Agent, or Firm* — Da Vinci Partners LLC; John Moetelli

(57) ABSTRACT

A temperature compensated bellows is provided for storage and displacement of a first fluid used as an indicator in a capillary tube. The bellows is made of a housing made of flexible, watertight material. The housing is made up of an upper portion, a lower portion, and an outer accordion formed portion. The accordion formed portion has a length/ and is sealingly connected along a periphery between the upper and lower portions. At least one entry/exit port formed on at least one of the portions thereof. At least one of the upper and lower portions extends from a periphery of the accordion formed portion substantially within the housing so as to reduce the storage volume. Preferably, within this area defined by the portion which extends within the housing, a temperature compensation device is disposed. This device is made up of a miniature bellows and reservoir in which a second fluid is placed having a coefficient of expansion which is different than the first fluid. The device is arranged to allow expansion of the second fluid to negatively affect the displacement of the first fluid in the (Continued)

capillary tube. In this manner, the appropriate selection of a first and second fluid allows for temperature compensation, so as to yield an indication which is consistent and accurate across a large range of temperatures.

8 Claims, 16 Drawing Sheets

(51) Int. Cl.
*G04B 1/26* (2006.01)
*A61M 5/14* (2006.01)

(56) References Cited

U.S. PATENT DOCUMENTS

| | | | | |
|---|---|---|---|---|
| 4,106,342 A | * | 8/1978 | Sormunen | G01L 7/06 73/386 |
| 4,967,609 A | * | 11/1990 | Takagi | F16D 3/845 277/636 |
| 6,274,254 B1 | * | 8/2001 | Abys | C25D 3/567 205/109 |
| 2005/0033232 A1 | | 2/2005 | Kriesel | |

OTHER PUBLICATIONS

International Search Report, International patent application No. PCT/IB2015/000446, dated Nov. 13, 2015.

* cited by examiner

A-A

B-B

Stroke compensation: comparison btw. measurements (ideal curve) and linearization (requirement)

US 10,815,032 B2

COMPENSATED CAPILLARY INDICATOR

CROSS REFERENCE TO RELATED APPLICATIONS

This application claims the benefit of U.S. Provisional Application No. 61/793,013, filed Mar. 15, 2015, and U.S. Provisional Application No. 61/623,160, filed Apr. 12, 2012, the contents of which are incorporated by reference hereto and relied upon.

COPYRIGHT & LEGAL NOTICE

A portion of the disclosure of this patent document contains material which is subject to copyright protection. The Applicant has no objection to the facsimile reproduction by anyone of the patent document or the patent disclosure as it appears in the Patent and Trademark Office patent file or records, but otherwise reserves all copyright rights whatsoever. Further, no references to third party patents or articles made herein is to be construed as an admission that the present invention is not entitled to antedate such material by virtue of prior invention.

BACKGROUND OF THE INVENTION

This invention relates to a bellows for storing and dispensing fluids in a controlled and consistent manner across a wide range of operating temperatures. In particular, the invention related to a bellows for storing and dispensing fluids in a capillary tube.

What is needed is a method of using one or more fluids in a capillary tube in manner which, in a simple arrangement, provides for reliable compensation for wide temperature fluctuations.

SUMMARY OF THE INVENTION

A temperature compensated bellows is provided for storage and displacement of a first fluid used as an indicator in a capillary tube. The principal bellows is made of a housing of flexible, watertight material. The housing is made up of an upper portion, a lower portion, and an outer accordion formed portion. The accordion formed portion has a length l and is sealingly connected along a periphery between the upper and lower portions. At least one entry/exit port is formed on at least one of the portions thereof. At least one of the upper and lower portions extends from a periphery of the accordion formed portion substantially within the housing so as to reduce the storage volume thereof. Preferably, within this area defined by the portion which extends within the housing, a temperature compensation device is disposed. This device is made up of a miniature bellows and reservoir in which a second fluid is placed having a coefficient of expansion which may be the same as or different than the first fluid. The device is arranged to allow expansion of the second fluid to negatively affect or compensate the displacement of the first fluid due to thermal expansion thereof in the capillary tube. In this manner, the appropriate selection of a first and second fluid allows for temperature compensation, so as to yield an indication (typically using the meniscus of the fluid contained in the capillary tube) which is consistent and accurate across a large range of temperatures.

An object of the invention is to enable indication using a single fluid in a capillary tube in manner which, in a simple arrangement, reliably compensates for wide temperature fluctuations.

Another object of the invention is to allow use of the fluids and two primary bellows with thermal compensation in order to increase the accuracy of indication of the meniscus thereof.

Those skilled in the art will appreciate that elements in the Figures are illustrated for simplicity and clarity and have not necessarily been drawn to scale. For example, dimensions may be exaggerated relative to other elements to help improve the understanding of the invention and its embodiments. Furthermore, when the terms 'first', 'second', and the like are used herein, their use is intended for distinguishing between similar elements and not necessarily for describing a sequential or chronological order. Moreover, relative terms like 'front', 'back', 'top' and 'bottom', and the like in the Description and/or in the claims are not necessarily used for describing exclusive relative position. Those skilled in the art will therefore understand that such terms may be interchangeable with other terms, and that the embodiments described herein are capable of operating in other orientations than those explicitly illustrated or otherwise described.

DETAILED DESCRIPTION OF THE PREFERRED EMBODIMENT

The following description is not intended to limit the scope of the invention in any way as they are exemplary in nature, serving to describe the best mode of the invention known the inventors as of the filing date hereof. Consequently, changes may be made in the arrangement and/or function of any of the elements described in the exemplary embodiments disclosed herein without departing from the spirit and scope of the invention.

Figure 1:
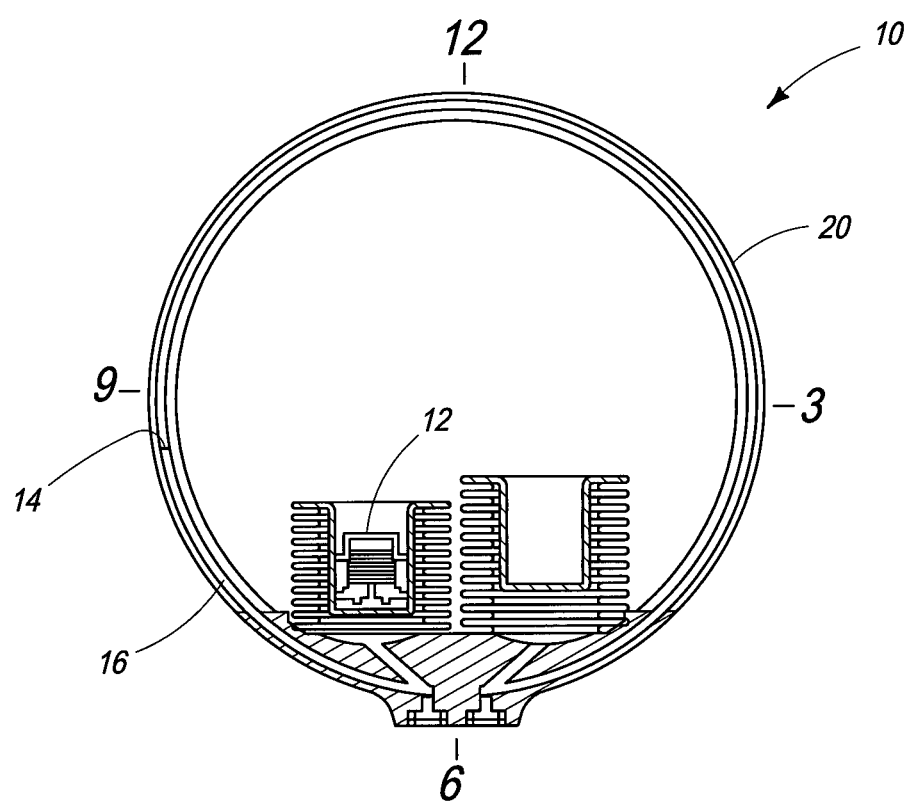
FIG. 1 is a plan view in partial cross-section of the invention applied to the indication of time.
Figure 2:
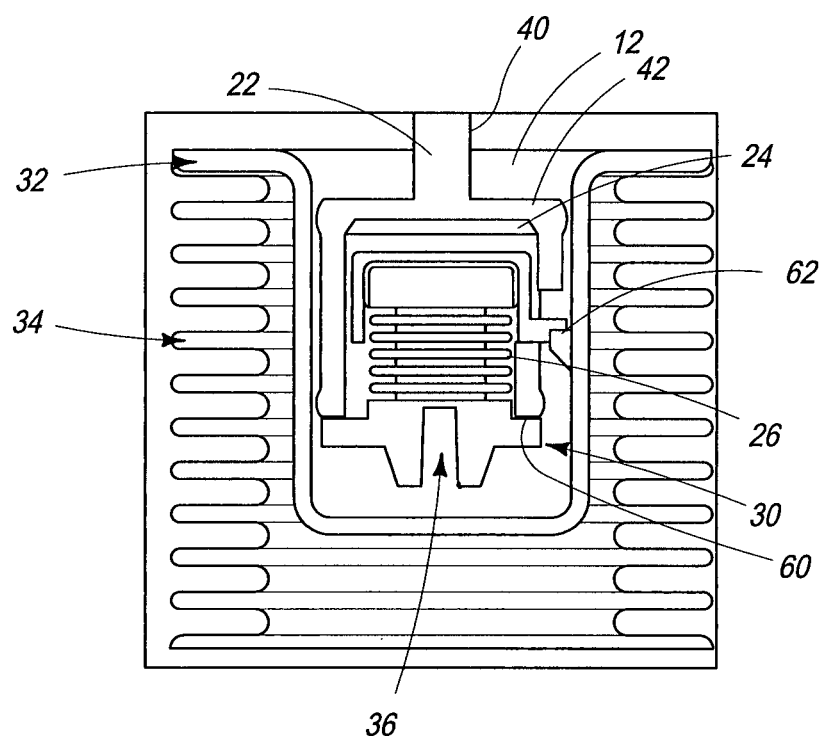
FIG. 2 is a cross-sectional view of the invention.

Referring now to FIGS. 1 and 2, a plan view of a system 10 in which temperature compensating device 12 of the invention is applied to maintain a position of a meniscus 14 of a fluid 16 in a capillary tube 20 across predictable temperature fluctuations. The invention 12 is particularly applicable to control the meniscus 14 of a fluid indicator of a fluid watch, such as that described in WO 2011/021097 A4, and U.S. Provisional Appl. No. 61/567,497, filed Dec. 6, 2011, the content of which are incorporated herein by reference thereto. In the foregoing, it is disclosed that the fluids may be liquids. Other applications of the device 12 of the invention may be envisioned. However, as an exemplary embodiment, the invention is applied to the indication of time in a wrist watch or a wall clock.

As can be seen, the fluid 16 enters the capillary tube 20 and consequently, its meniscus 14, indicates time (9, 12, 3 and 6 o'clock) when joined with a watch mechanism which raises the stem at a prescribed rate. Where there are significant temperature variations, inaccuracies in the position of the meniscus 14 are introduced. The temperature compensation subsystems described hereinbelow mitigate the error introduced by temperature flux in order to provide a more reliable indication of time over a large temperature variation. Indeed, with these subsystems of the invention, the capillary tube 20 may have an open end (not shown), because only one fluid 16 need be used therein, which enables a simplification of the entire mechanism.

Figure 3:
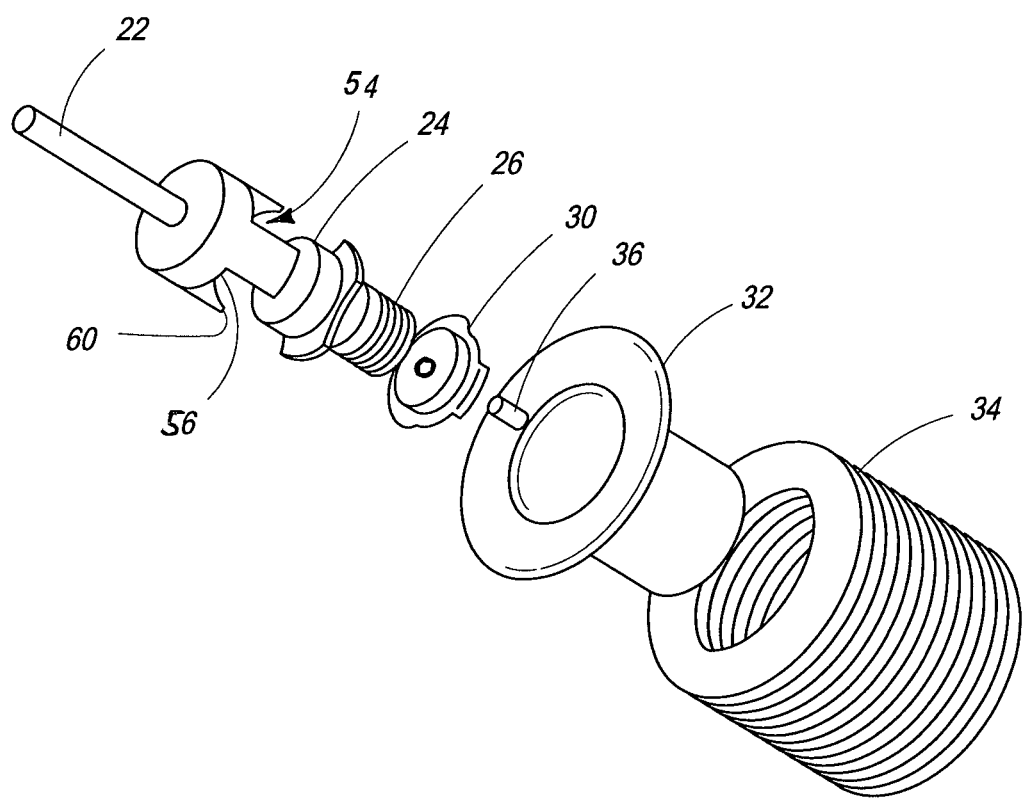
FIG. 3 is an exploded view of the invention.

Referring in particular to FIG. 2, the temperature compensating device 12 includes a piston 22, a top cap 24, a small bellows 26, a bottom cap 30, which interface with a internal, recessed cap 32 of the large bellows 34, and a sealing pin 36. The piston 22, best seen in FIG. 3 has a stem 40 attached to a segmented cup 42, into which the temperature compensating bellows subassembly 12 mounts.

Figure 4B:
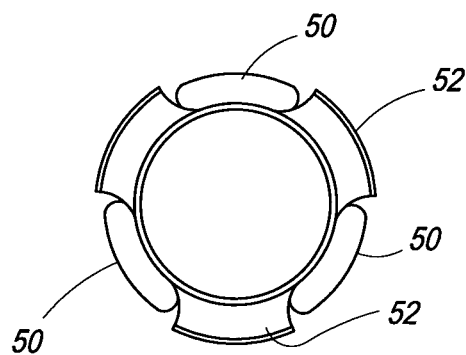
FIG. 4B is a top view of the temperature compensating bellows subassembly of the invention
Figure 4C:
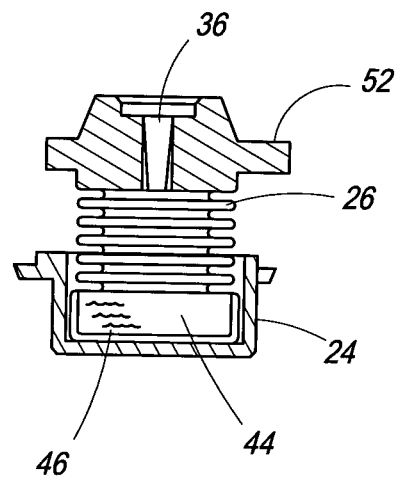
FIG. 4C is a cross sectional view of the temperature compensating bellows subassembly of the invention
Figure 4A:
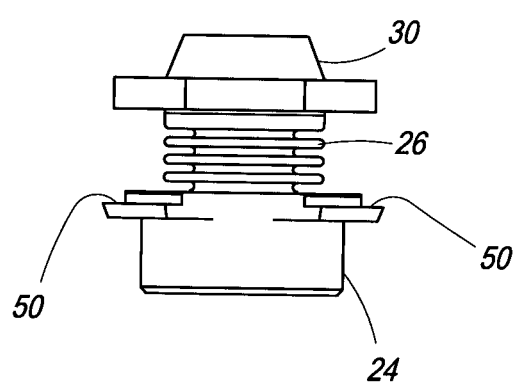
FIG. 4A is a side view of a temperature compensating bellows subassembly of the invention.

Referring now to FIGS. 4A to 4C, the temperature compensating bellows subassembly 12 includes the top cap 24, small bellows 26, bottom cap 30, and the sealing pin 36. The top cap 24, small bellows 26, bottom and cap 30 are sealed together by laser welding or other known methods, so as to create an internal volume 44 that, when the sealing pin 36 is in place, is suitable for containing a compensating fluid 46. The top cap 24 has three tangs 50 or partial flanges which extend into segmentations 54 of the cup 42 of the piston 22 and bear against surfaces 56 thereof. The bottom cap 30 has three tangs 52 that extend so as to interface with the end surfaces 60 of the cup 42 of the piston 22. This arrangement essentially provides for a temperature compensated interface with tangs 62 of the external recessed cup 32 of the large bellows 34. Proper sizing of the components, along with the selection of the appropriate compensating fluid 46, enables the temperature compensating bellows subassembly 12 of the invention to counteract the effects of temperature fluctuations.

Figure 5C:
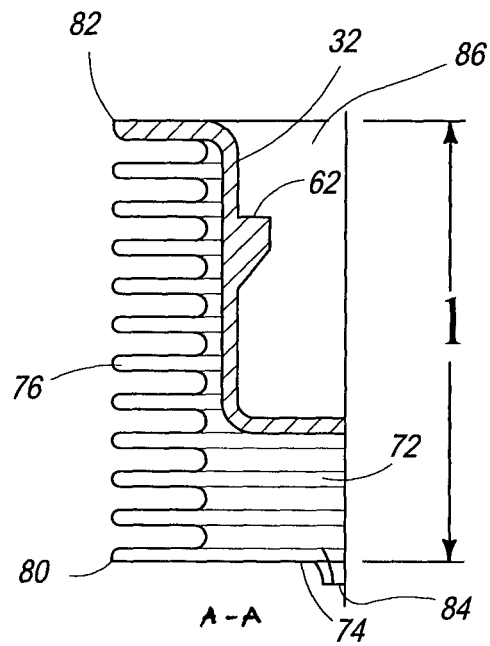
FIG. 5C is a partial cross sectional view of the principal bellows used in the temperature compensated bellows of the invention.
Figure 5B:
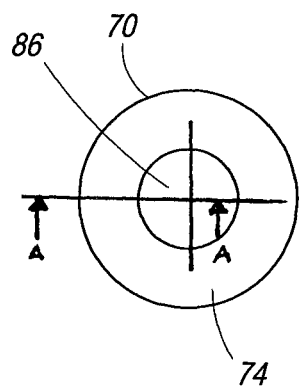
FIG. 5B is a top view of the principal bellows used in the temperature compensated bellows of the invention.
Figure 5A:
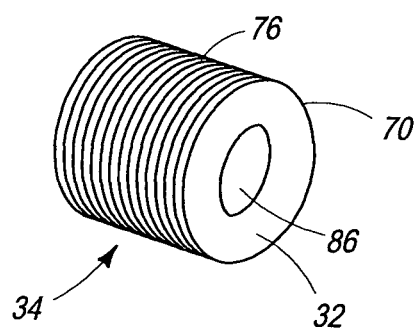
FIG. 5A is a perspective view of a principal bellows used in the temperature compensated bellows of the invention.

Referring now to FIGS. 5A-5C, the large bellows 34 is provided for fluid storage and displacement used in precise fluid indication in the capillary tube 20. The bellows 34 is made of a housing 70 made of flexible, watertight material. The housing 70 encloses the principal reservoir 72 and is made up of the external recessed cap 32, a lower portion 74, and an outer accordion formed portion 76. The accordion formed portion 76 has a length l and is sealingly connected along a periphery 22 and 24 between the recessed cap 32 and the lower portions 74. At least one entry/exit port 84 is formed on at least one of the portions thereof. At least one of the upper and lower portions 32 or 74 extends from a periphery 80, 82 of the accordion formed portion 76 substantially within the housing 70 so as to create a recess 28 which reduces the storage volume. In the relaxed condition, the bellows 34 is collapsed.

Figure 6:
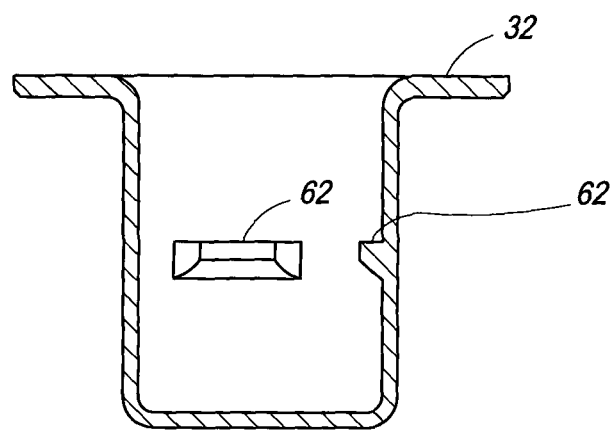
FIG. 6 is a cross-sectional view of the portion of the principal bellows which extends within the bellows body, and into which the compensating bellows subassembly mounts.

Referring now to FIG. 6, the tangs 62 formed on the upper portion 32, against which the tangs 52 of the bottom cap 30 interface are more clearly shown. The upper portion has a base from which a cylindrical wall extends, to a flange. The tangs 62 are formed on the internal diameter of the cylindrical wall and do not extend fully circumferentially about those the wall.

Figure 7C:
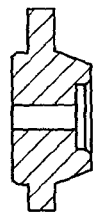
FIG. 7C is a cross-sectional view of the bottom cap of the compensating bellows subassembly of the invention.
Figure 7B:
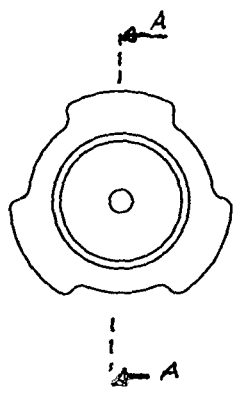
FIG. 7B is a top view of the bottom cap of the compensating bellows subassembly of the invention.
Figure 7A:
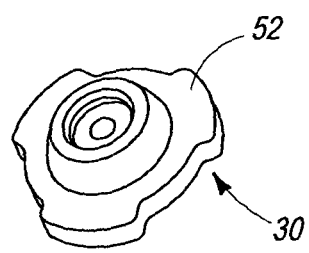
FIG. 7A is a perspective view of a bottom cap of the compensating bellows subassembly of the invention.

Referring now to FIG. 7A to 7C, the bottom cap 30 is shown in more detail. A central, axially located aperture receives the sealing pin 36. Tangs 52 extend from a base and encompass approximately 60 degrees of the circumference thereof. A lower lip of the small bellows 26 sealingly interfaces with the lower surface of the bottom cap 30.

Figure 8:
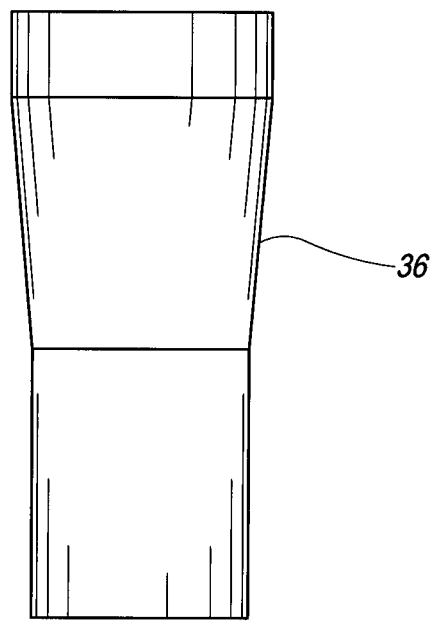
FIG. 8 is a side view of a sealing pin of the compensating bellows subassembly of the invention.

Referring now to FIG. 8, the sealing pin 36 is shown in more detail. The sealing pin 36 is cylindrical in form, having a tapered portion to better seal against the aperture of the bottom cap 30.

Figure 9:
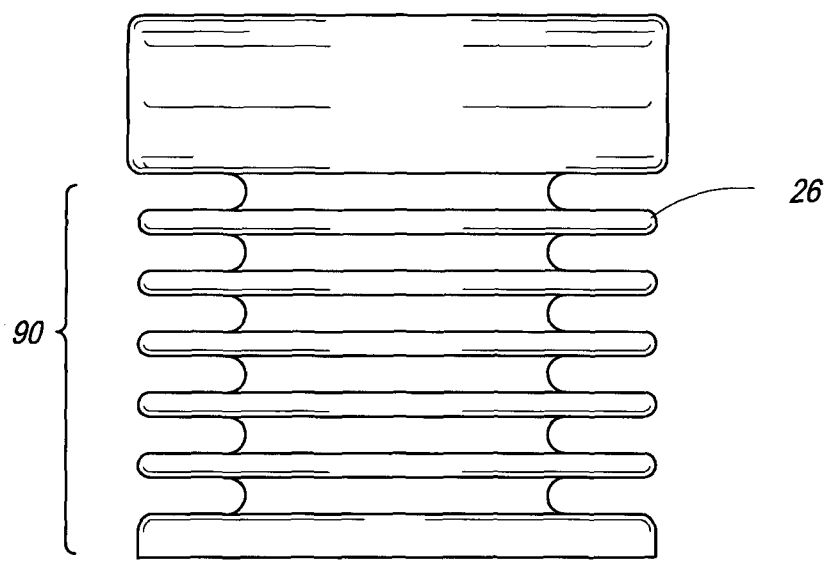
FIG. 9 is a side view of a compensating bellows of the compensating bellows subassembly of the invention.

Referring now to FIG. 9, the small bellows 26, including its accordion portion 90 is shown in more detail.

Figure 10C:
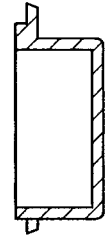
FIG. 10C is a cross-sectional view of the top cap of the compensating bellows subassembly of the invention.
Figure 10B:
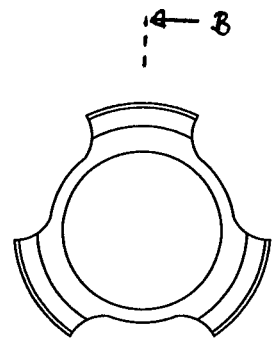
FIG. 10B is a top view of the top cap of the compensating bellows subassembly of the invention.
Figure 10A:
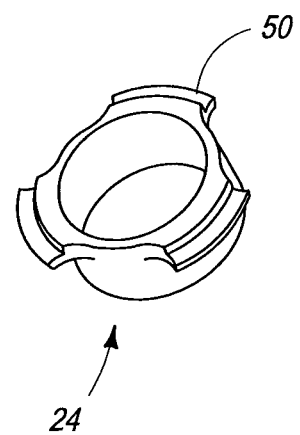
FIG. 10A is a perspective view of a top cap of the compensating bellows subassembly of the invention.

Referring now to FIGS. 10A to 10C, the top cap 24 is shown in more detail. The upper portion has a base from which a cylindrical wall extends, to the tangs 50 thereof. The tangs 50 extend approximately 60 degrees about its periphery.

Figure 11:
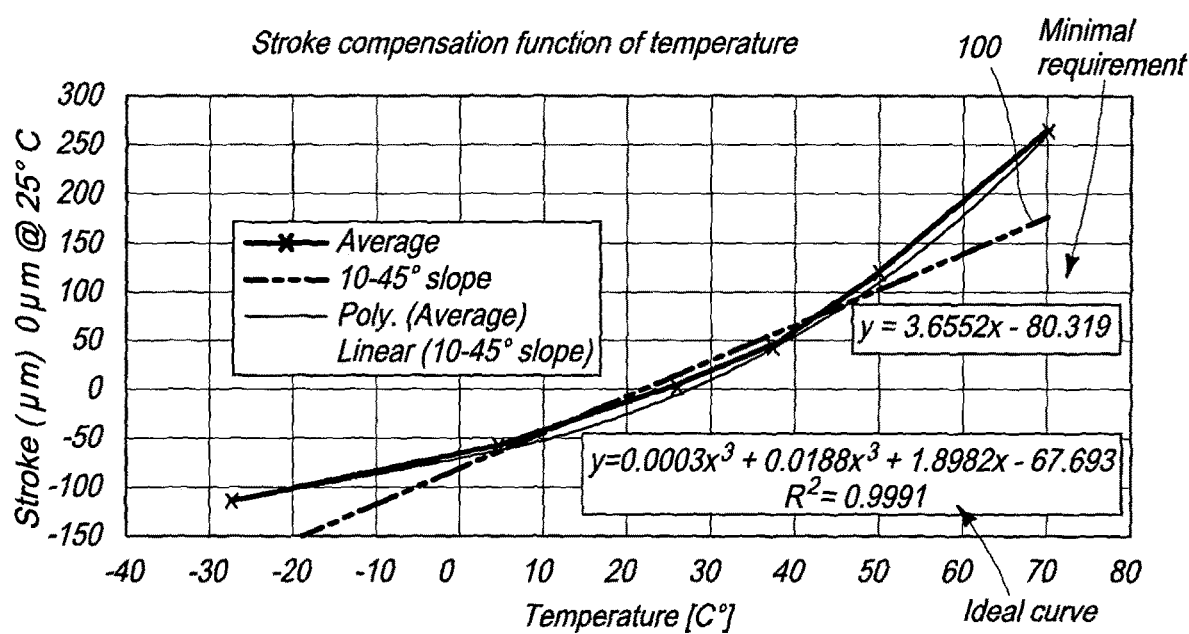
FIG. 11 is a table of stroke compensation which is the purpose of the compensating bellows subassembly of the invention.

Referring now to FIG. 11, in one embodiment, the temperature compensating bellows subassembly 12 of the invention approximates a stroke compensation curve in order to accurately compensate for temperature variations in a working range from minus 20 degrees to plus 70 degrees Celsius. The rate of displacement of the piston 22 vs. temperature is approximately 3.65 micrometers per degree Celsius. For safe operation, the fluid 46 used in the bellows 26 should be non-toxic.

Figure 12:
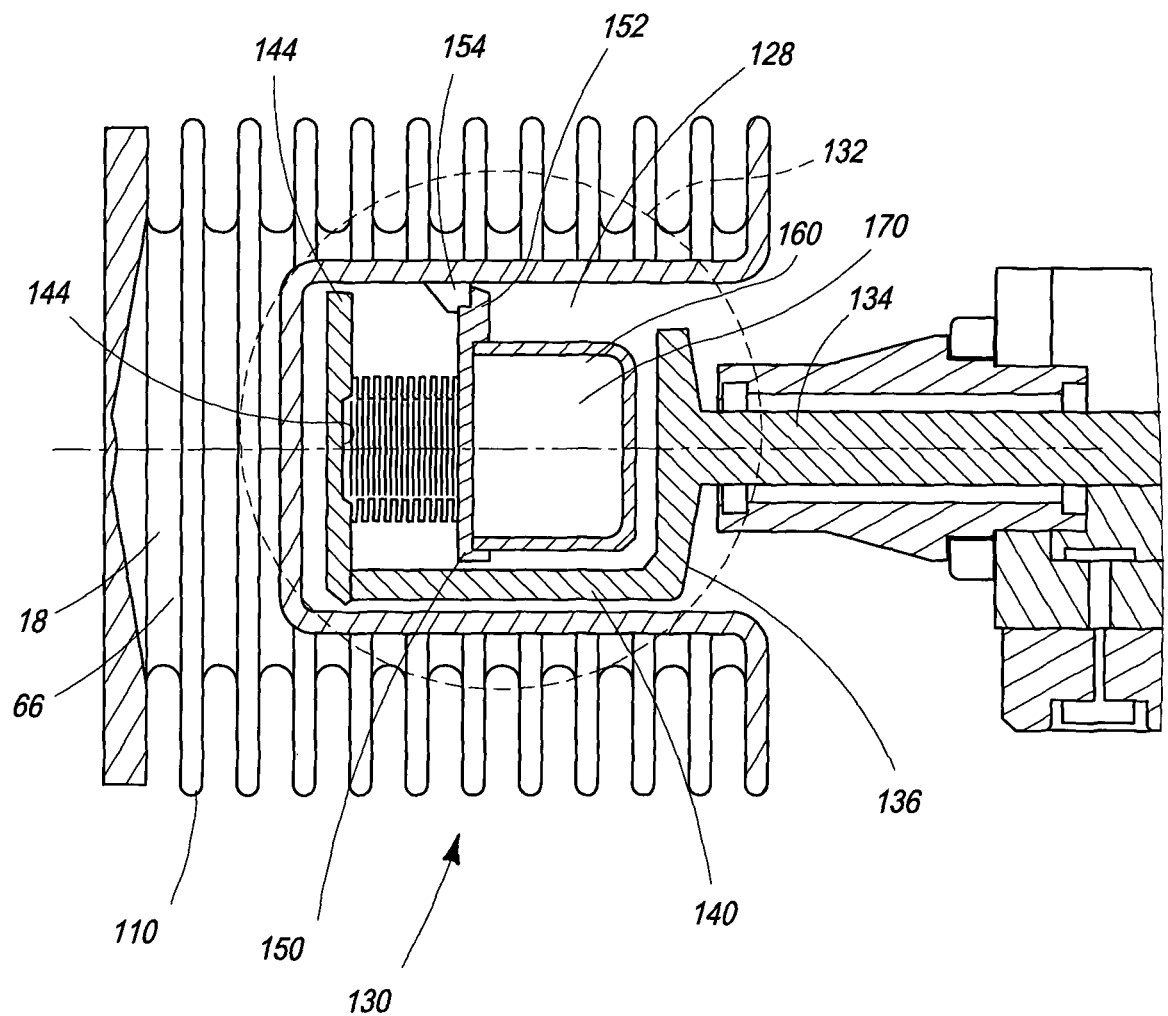
FIG. 12 is a cross-sectional view of an alternate embodiment of the temperature compensating bellows subassembly of the invention.
Figure 13:
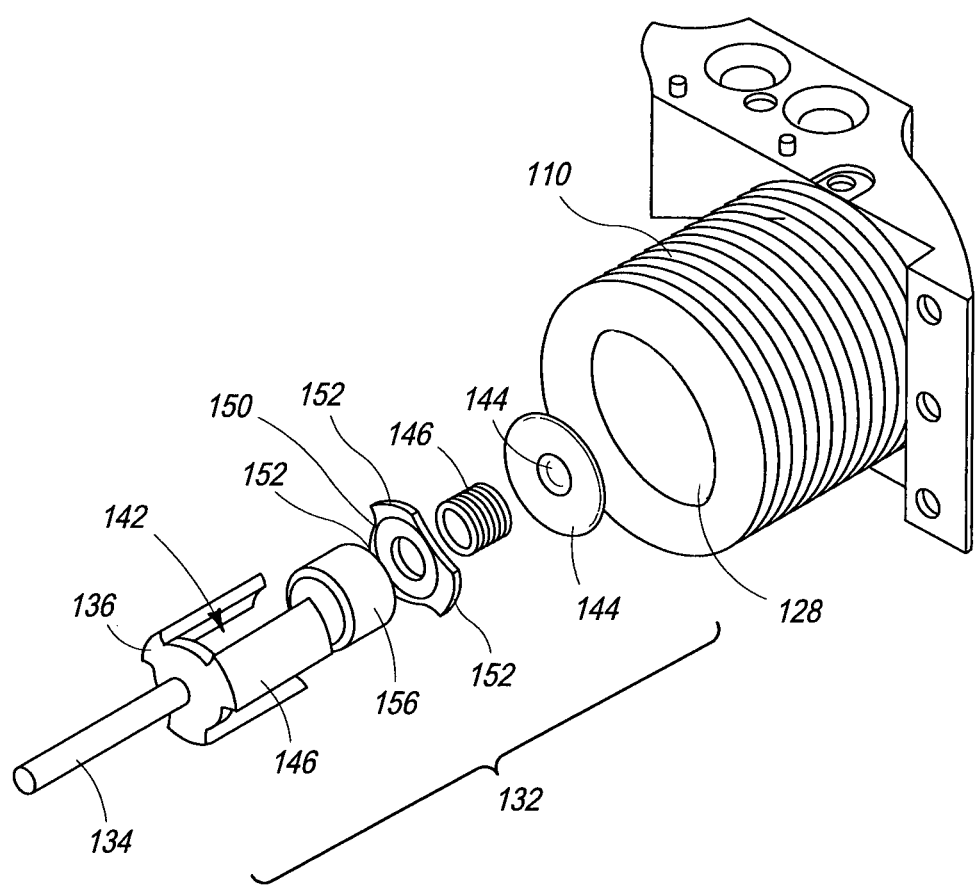
FIG. 13 is an exploded view of the alternate embodiment of the temperature compensated bellows of FIG. 12.

Referring now to FIGS. 12 and 13, the temperature compensated bellows system 130 includes a temperature compensating subsystem 132. The temperature compensating subsystem 132 includes a modified stem 134 having a primary support flange 136 on which a cylindrical casing 40 is formed. The cylindrical casing 140 has reliefs 142. A cap 144 spans the cylindrical casing 140 and is glued or welded thereto. A recess 44 centers and receives a miniature bellows 146 which is welded or glued to a flange 150 having two or more evenly distributed tangs 152 which engage bellows interface tabs 154 on the primary bellows 110. A supplemental housing 156 is welded or glued to and in fluid communication with the mini bellows 146, to form a reservoir 160. In operation, the invention 130 mitigates inaccuracies of a position of the meniscus 162 (See FIG. 1) in a capillary tube 20 by countering the effect of thermal expansion of the first fluid 16 in the bellows 110. This countering or mitigation is accomplished by placing a second fluid 170 in the reservoir 160 which has the selected coefficient of expansion necessary to compensate for the thermal expansion of the first fluid 166.

Figure 14A:
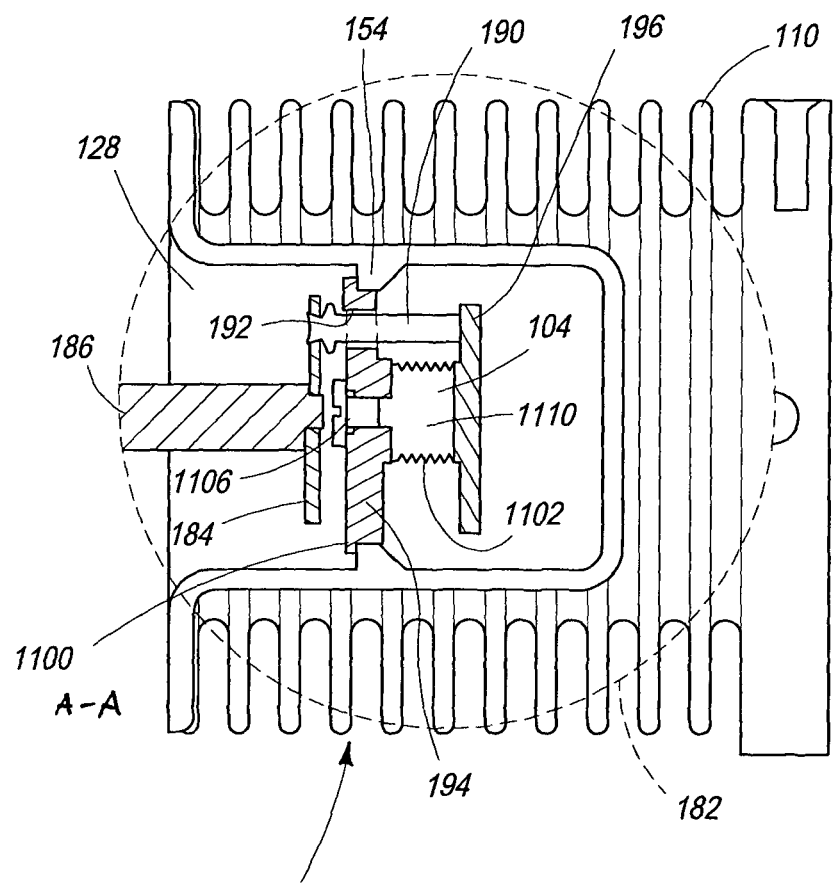
FIG. 14A is cross-sectional side view of a first alternate embodiment of the invention.
Figure 14B:
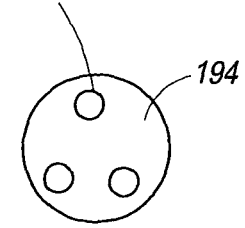
FIG. 14B is a partial top view showing a hole pattern in a component of the invention.

Referring now to FIG. 14A, in an alternate embodiment 180, an alternate temperature compensating subsystem 182 includes a first flange 184 attached to the stem 186. The first flange 184 has at least two standoffs 190 attached thereto and extending through apertures 192 in a second flange 194, to a cap 196. The second flange 194 has at least two tangs 1100 which interface with bellows interface tabs 154. A mini bellows 1102 is sealingly captured between the cap 196 and the second flange 194 and encloses a second fluid 1104. A plug 1106 permits filling of the reservoir 1110, enclosed by the mini bellows 1102. In operation, heat influences cause expansion of the second fluid 1104 so as to mitigate the heat expansion effects of the first fluid 166. FIG. 14B schematically shows the holes 192 for the pins 190 in the plate 194.

Below is a sample calculation of thermal expansion based on the selection of ethanol as a fluid. As can be seen, the same fluid can be used for fluid one and two 166 and 1104 respectively, if the volume and geometry of the primary and compensating reservoirs 118 and 1110 respectively are comparable. Further, if fluids 166 and 1104 having largely different values of thermal expansion are used, the volume and geometry of the reservoirs can be significantly different.

Below are sample calculations:

$r_3 := 0.9$ mm $S_{31} := \pi \cdot r_3^2 = 2.545$ mm² Surface of the fluid cylinder (according to drawing)

$h_{31} := 1.2$ mm Height of the fluid cylinder (according to drawing)

$V_{30} := S_{31} \cdot h_{31} = 3.054$ mm³ Fluid volume $\beta := \beta_{ethanol}$ $\Delta V_3 := V_{30} \cdot \beta \cdot \Delta T = 0.057$ mm³

$\Delta L_{solution3} := \Delta V_3 / S_{31} = 22.5$ μm

Figure 15:
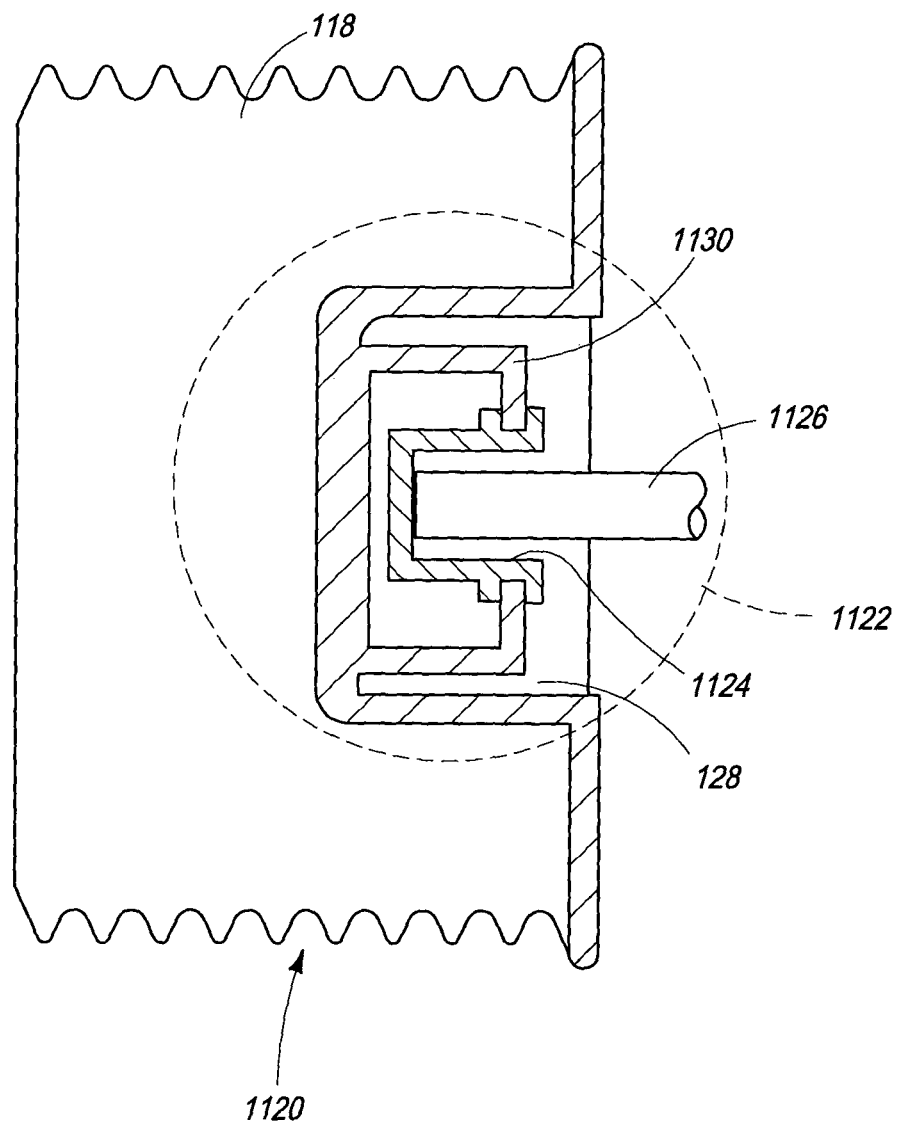
FIG. 15 is a cross-sectional view of a second alternate embodiment of the invention.

Referring now to FIG. 15, a further alternate embodiment 1120 having an alternate subsystem 1122 is shown which does not use fluid but instead, materials having a suitable coefficient of thermal expansion. Here a first flanged cap 1124 interfaces on the one hand with the stem 1126 and on the other hand, with a second flanged cap 1130 which on another end, interfaces with the bellows 110. The first and second flanged caps 1124 and 1126 are made of materials having coefficients of thermal expansion selected to compensate for indication error caused by thermal expansion of the first fluid 166.

Figure 16:
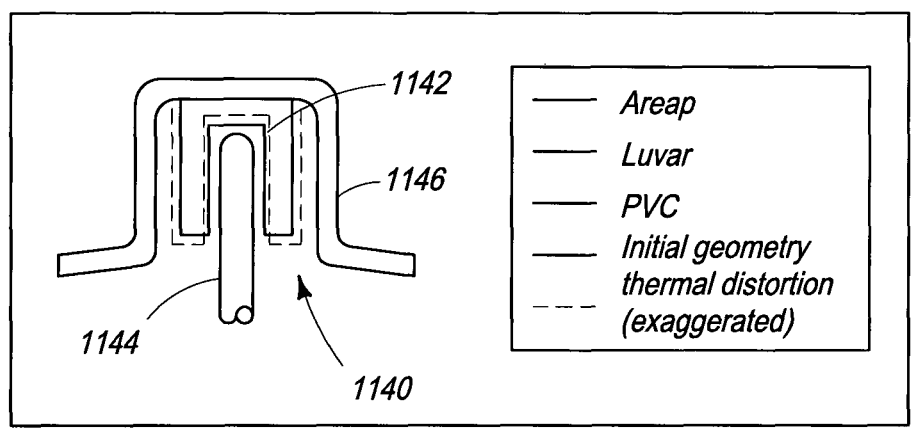
FIG. 16 is cross-sectional view of a fourth alternate embodiment of the invention.

Referring now to FIG. 16, a further alternate configuration 140 is the same as the previous embodiment, except that a further cap 142 is introduced between the stem 144 and the second flanged cap 124.

A sample calculation using materials having very different coefficients of thermal expansion (invar and PVC) yield the following values:

$$L_{invar} := 4.7 \text{ mm} \quad \alpha_{invar} := \frac{1.2e-6}{K}$$

$$L_{PVC} := 3.7 \text{ mm} \quad \alpha_{PVC} := \frac{5e-5}{K}$$

-continued $$\Delta L_{invar} := L_{invar} \cdot \alpha_{invar} \cdot \Delta T = 0.141 \text{ μm}$$

$$\Delta L_{PVC} := L_{PVC} \cdot \alpha_{PVC} \cdot \Delta T = 4.625 \text{ μm}$$

$$\Delta L_{Solution1} := -\Delta L_{invar} + \Delta L_{PVC} = 4.484 \text{ μm}$$

Note that the above calculations are approximate in which ideal conditions are assumed. Further, the effect of other components are not considered and do influence the final position of the indication miniscus. Further, the thermal expansion of other elements, geometric deformation, flexibility of the materials, tolerances and a safety factor is not considered.

In one embodiment, the bellows is made of brass.

In another embodiment, the bellows is made of copper.

In another embodiment, the bellows is made of beryllium copper.

The bellows may optionally be coated with a brilliant coating such as gold.

It should be appreciated that the particular implementations shown and herein described are representative of the invention and its best mode and are not intended to limit the scope of the present invention in any way.

It should be appreciated that many applications of the present invention may be formulated.

As will be appreciated by skilled artisans, the present invention may be embodied as a system, a device, or a method.

Moreover, the system contemplates the use, sale and/or distribution of any goods, services or information having similar functionality described herein.

The specification and figures should be considered in an illustrative manner, rather than a restrictive one and all modifications described herein are intended to be included within the scope of the invention claimed. Accordingly, the scope of the invention should be determined by the appended claims (as they currently exist or as later amended or added, and their legal equivalents) rather than by merely the examples described above. Steps recited in any method or process claims, unless otherwise expressly stated, may be executed in any order and are not limited to the specific order presented in any claim. Further, the elements and/or components recited in apparatus claims may be assembled or otherwise functionally configured in a variety of permutations to produce substantially the same result as the present invention. Consequently, the invention should not be interpreted as being limited to the specific configuration recited in the claims.

Benefits, other advantages and solutions mentioned herein are not to be construed as critical, required or essential features or components of any or all the claims.

As used herein, the terms "comprises", "comprising", or variations thereof, are intended to refer to a non-exclusive listing of elements, such that any apparatus, process, method, article, or composition of the invention that comprises a list of elements, that does not include only those elements recited, but may also include other elements described in the instant specification. Unless otherwise explicitly stated, the use of the term "consisting" or "consisting of" or "consisting essentially of" is not intended to limit the scope of the invention to the enumerated elements named thereafter, unless otherwise indicated. Other combinations and/or modifications of the above-described elements, materials or structures used in the practice of the present invention may be varied or adapted by the skilled artisan to other designs without departing from the general principles of the invention.

The patents and articles mentioned above are hereby incorporated by reference herein, unless otherwise noted, to the extent that the same are not inconsistent with this disclosure.

Other characteristics and modes of execution of the invention are described in the appended claims.

Further, the invention should be considered as comprising all possible combinations of every feature described in the instant specification, appended claims, and/or drawing figures which may be considered new, inventive and industrially applicable.

Copyright may be owned by the Applicant(s) or their assignee and, with respect to express Licensees to third parties of the rights defined in one or more claims herein, no implied license is granted herein to use the invention as defined in the remaining claims. Further, vis-à-vis the public or third parties, no express or implied license is granted to prepare derivative works based on this patent specification.

Multiple variations and modifications are possible in the embodiments of the invention described here. Although certain illustrative embodiments of the invention have been shown and described here, a wide range of changes, modifications, and substitutions is contemplated in the foregoing disclosure. While the above description contains many specific details, these should not be construed as limitations on the scope of the invention, but rather exemplify one or another preferred embodiment thereof. In some instances, some features of the present invention may be employed without à corresponding use of the other features. Accordingly, it is appropriate that the foregoing description be construed broadly and understood as being illustrative only, the spirit and scope of the invention being limited only by the claims which ultimately issue in this application.

What is claimed is:

1. A bellows assembly for storage and displacement of a first liquid having a direction of thermal expansion and used in precise liquid indication in a capillary tube, the bellows assembly comprising:
   a. a first bellows housing for storing the first liquid contained therein in a storage volume capable of expanding only in a first relative direction, the first liquid expanding in the first relative direction, the housing made of a flexible, water-tight material and comprising:
      i. an upper portion,
      ii. a lower portion,
      iii. an outer accordion portion having a length l and sealingly connected along a periphery with the upper and lower portions, and
      iv. at least one entry/exit port formed on at least one of the portions thereof, and
   b. a temperature compensation device including a second bellows capable of expanding only in a second relative direction different than the first relative direction, the second bellows containing a second liquid which thermally expands in the second relative direction other than the first relative direction of thermal expansion of the first liquid in the first bellows, the temperature compensation device comprising:
      i. a second bellows housing,
      ii. the second liquid contained in the second bellows housing which thermally expands in the second relative direction at a second expansion rate, and
      iii. a support arrangement for the second bellows housing such that the thermal expansion of the first liquid which causes an expansion of the first liquid at a first expansion rate in the capillary tube in the first relative direction is mitigated by the deformation of the second bellows due to the thermal expansion of the second liquid at a second expansion rate in the second relative direction.

2. The bellows assembly of claim 1, wherein at least one of the upper and lower portions extends within the housing so as to reduce the storage volume in the housing.

3. The bellows assembly of claim 1, wherein the first and second expansion rates are comparable.

4. The bellows assembly of claim 1, wherein the first and second expansion rates are different.

5. The bellows assembly of claim 1, wherein at least the outer accordion portion is made of brass.

6. The bellows assembly of claim 1, wherein at least the outer accordion portion is made of copper.

7. The bellows assembly of claim 1, wherein at least the outer accordion portion is made of beryllium copper.

8. The bellows assembly of claim 1, wherein at least the outer accordion portion is coated with a gold coating.

* * * * *